(12) United States Patent
Braun et al.

(10) Patent No.: US 9,144,610 B2
(45) Date of Patent: Sep. 29, 2015

(54) POLYMERIC THICKENING AGENT FREE OF ACRYLAMIDE FRAGMENTS, METHOD FOR THE PREPARATION THEREOF, AND COMPOSITION CONTAINING SAME

(75) Inventors: Olivier Braun, Castres (FR); Paul Mallo, Croissy-sur-Seine (FR)

(73) Assignee: SOCIETE D'EXPLOITATION DE PRODUITS POUR LES INDUSTRIES CHIMIQUES SEPPIC, Paris (FR)

( * ) Notice: Subject to any disclaimer, the term of this patent is extended or adjusted under 35 U.S.C. 154(b) by 33 days.

(21) Appl. No.: 13/878,604

(22) PCT Filed: Nov. 16, 2011

(86) PCT No.: PCT/FR2011/052648
§ 371 (c)(1),
(2), (4) Date: Apr. 10, 2013

(87) PCT Pub. No.: WO2012/072911
PCT Pub. Date: Jun. 7, 2012

(65) Prior Publication Data
US 2013/0190410 A1 Jul. 25, 2013

(30) Foreign Application Priority Data
Nov. 30, 2010 (FR) ..................................... 10 59944

(51) Int. Cl.
| | |
|---|---|
| *A61K 47/32* | (2006.01) |
| *A61K 8/81* | (2006.01) |
| *A61Q 19/00* | (2006.01) |
| *C08F 2/32* | (2006.01) |
| *A61K 8/06* | (2006.01) |
| *A61Q 17/04* | (2006.01) |
| *A61Q 1/02* | (2006.01) |
| *A61Q 1/08* | (2006.01) |
| *A61Q 1/14* | (2006.01) |
| *A61Q 5/00* | (2006.01) |
| *A61Q 5/02* | (2006.01) |
| *A61Q 5/12* | (2006.01) |
| *A61Q 19/06* | (2006.01) |
| *A61Q 19/10* | (2006.01) |
| *C08F 220/06* | (2006.01) |

(52) U.S. Cl.
CPC .................. *A61K 47/32* (2013.01); *A61K 8/064* (2013.01); *A61K 8/8152* (2013.01); *A61K 8/8164* (2013.01); *A61Q 19/00* (2013.01); *C08F 2/32* (2013.01); *A61K 2800/10* (2013.01); *A61Q 1/02* (2013.01); *A61Q 1/08* (2013.01); *A61Q 1/14* (2013.01); *A61Q 5/002* (2013.01); *A61Q 5/02* (2013.01); *A61Q 5/12* (2013.01); *A61Q 17/04* (2013.01); *A61Q 19/002* (2013.01); *A61Q 19/004* (2013.01); *A61Q 19/06* (2013.01); *A61Q 19/10* (2013.01); *C08F 220/06* (2013.01)

(58) Field of Classification Search
CPC ......... C08F 220/06; C08F 2/32; A61K 8/064; A61K 8/8152; A61K 8/8164
USPC .................................... 514/772.6, 772.4, 557
See application file for complete search history.

(56) References Cited

U.S. PATENT DOCUMENTS

| | | | |
|---|---|---|---|
| 4,284,708 A | 8/1981 | Helling et al. | |
| 4,359,564 A * | 11/1982 | Merritt et al. | 526/260 |
| 2007/0219315 A1* | 9/2007 | Braun | 524/801 |
| 2012/0100084 A1 | 4/2012 | Peter et al. | |

FOREIGN PATENT DOCUMENTS

| | | | |
|---|---|---|---|
| DE | 10 2009 014877 | 9/2009 | |
| EP | 0 017 025 | 10/1980 | |
| EP | 0 010 708 | 8/1982 | |
| WO | WO 00/32639 * | 6/2000 | C08F 2/32 |

OTHER PUBLICATIONS

International Search Report dated Jan. 13, 2012, in corresponding PCT application.

* cited by examiner

*Primary Examiner* — Anna Falkowitz
(74) *Attorney, Agent, or Firm* — Young & Thompson

(57) ABSTRACT

A composition including an oil phase, an aqueous phase, at least one water-in-oil emulsifying system in the form of a positive latex, characterized in that the composition includes a straight, branched, or cross-linked anionic polyelectrolyte, including: a) a non-zero molar proportion of monomer units from acrylic acid in free or partially salified form; and b) a non-zero molar proportion of monomer units from the acid of formula (I):

$$CH_2=CH-C(=O)-O-[CH_2-CH2-C(=O)-O]_n-H \quad (I),$$

where n is a number greater than or equal to (1) and less than or equal to (5), in free or partially salified form. A method for preparing the same, a polymer powder, and the use thereof as a thickening agent for cosmetic or pharmaceutical compositions are also described.

11 Claims, No Drawings

POLYMERIC THICKENING AGENT FREE OF ACRYLAMIDE FRAGMENTS, METHOD FOR THE PREPARATION THEREOF, AND COMPOSITION CONTAINING SAME

The subject of the invention is novel polymeric anionic thickeners, the process for preparing same and also the use thereof as a thickener and/or emulsifier.

The thickening of aqueous phases is generally carried out by incorporating therein hydrophilic polymers of all types, whether there are synthetic or of natural origin.

Among the polymers of natural origin, xanthan or guar gums are quite widely used. However, they have the conventional drawbacks of natural products, namely fluctuating quality and price.

Among the hydrophilic synthetic thickeners most widely used are polymers in the form of powders or of self-invertible inverse latexes. In terms of chemical structure, they are in particular acrylic acid homopolymers in free or partially salified form; homopolymers in free form are generally synthesized by precipitation polymerization and are in powder form; as for homopolymers in partially salified form, they are generally prepared either by precipitation polymerization or by inverse emulsion polymerization. There are, for example, the self-invertible inverse latexes disclosed in the European patent application published under number EP 1 010 708 A1, in which the acrylic acid homopolymer is salified in the form of an ammonium salt or of a monoethanolamine salt. However, the thickening power of the polymers of this first family is not entirely satisfactory and their unpleasant odor due to the presence of a nitrogenous base limits their use in the cosmetics industry. The European patent application published under number EP 0 17 025 A1 discloses copolymers of acrylic acid with acrylic acid dimer which are used as photographic film layers. The German patent application published under number DE 10 2009 014 877 A1 discloses copolymers of 2-acrylamido-1-methylpropanesulfonic acid and carboxyethylacrylate which are used in the cosmetics industry.

The inventors have sought to develop thickening polymers which have a better thickening power than the acrylic polymers of the prior art and which do not have this drawback in terms of unpleasant odor.

According to a first aspect, a subject of the invention is a composition comprising an oil phase, an aqueous phase and at least one water-in-oil emulsifying system, in the form of an inverse latex, characterized in that it comprises a linear, branched or crosslinked anionic polyelectrolyte, comprising:
 a) a non-zero molar proportion of monomeric units resulting from acrylic acid in free or partially salified form, and
 b) a non-zero molar proportion of monomeric units resulting from the acid of formula (I):

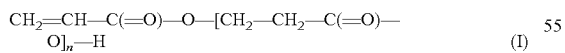

$$CH_2=CH-C(=O)-O-[CH_2-CH_2-C(=O)-O]_n-H \quad (I)$$

in which n represents a number greater than or equal to 1 and less than or equal to 5, or from a mixture of acids of formula (I), in free or partially salified form.

The term "inverse latex" denotes a water-in-oil emulsion of at least one polymer.

The term "branched polyelectrolyte" denotes a nonlinear polyelectrolyte which has pendant chains so as to obtain, when it is dissolved in water, a highly entangled state resulting in very high viscosities at low rate gradient.

The term "crosslinked polyelectrolyte" denotes a nonlinear polyelectrolyte which is in the form of a three-dimensional network that is water-insoluble but water-swellable and therefore results in the attainment of a chemical gel.

In the definition of the inverse latex as previously defined, the term "salified" indicates that it involves alkali metal salts such as sodium or potassium salts.

The constituent polyelectrolyte of said inverse latex may comprise crosslinked units and/or branched units.

In the composition as defined above, the "water-in-oil" (W/O) emulsifying system consists either of a single surfactant or of a mixture of surfactants, on the condition that said surfactant or said mixture has an HLB value sufficiently low to induce a water-in-oil emulsion. Mention is made, for example, of sorbitan esters, for instance sorbitan oleate, sold by the company SEPPIC under the name Montane™ 80, sorbitan isostearate, sold by the company SEPPIC under the name Montane™ 70 or sorbitan sesquioleate sold by the company SEPPIC under the name Montane™ 83. Mention is also made of certain polyethoxylated sorbitan esters, for example the pentaethoxylated sorbitan monooleate sold by the company SEPPIC under the name Montanox™ 81 or the pentaethoxylated sorbitan isostearate sold under the name Montanox™ 71 by the company SEPPIC. Mention is also made of polyesters having a molecular weight of between 1000 and 3000, produced from condensation between a poly(isobutenyl)succinic acid or its anhydride and such as Hypermer™ 2296 sold by the company Uniqema or, finally, block copolymers having a molecular weight between 2500 and 3500, for instance Hypermer™ B246 sold by the company Uniqema or Simaline™ IE 200 sold by the company SEPPIC.

The composition as previously defined generally comprises between 0.5% by weight and 10% by weight of said "water-in-oil" emulsifying system.

The inverse latex generally comprises, for 100% by weight, from 1% to 50% by weight of water.

The oil phase of the self-invertible inverse latex described above is made up:
 either of a mineral oil, or of a mixture of mineral oils, containing saturated hydrocarbons of paraffin, isoparaffin or cycloparaffin type, having, at ambient temperature, a density between 0.7 and 0.9 and a boiling point above 180° C., such as, for example, Isopar™ M or Isopar™ L, Exxol™ D 100 S sold by Exxon or the mineral white oils in accordance with the FDA 21 CFR 172.878 and FR 178.3620(a) regulations, such as Marcol™ 52 or Marcol™ 82, also sold by Exxon;
 or of a synthetic oil, or of a mixture of synthetic oils, such as hydrogenated polyisobutenes, in particular those sold in France by the company Ets B. Hossow and Cie under the name Parleam-Polysynlane™ and cited in Michel and Irene Ash; Thesaurus of Chemical products, Chemise Publicité Cos, Ince. 1986 Volume I, page 211 (ISBN 0 7131 36030); polydecenes; isohexa-decane, identified in Chemical Abstracts by the number RN=93685-804 and which is a mixture of $C_{12}$, $C_{16}$ and $C_{20}$ isoparaffins containing at least 97% of $C_{16}$ isoparaffins, among which the main constituent is 2,2,4,4,6,8,8-heptamethylnonane (RN=4390-04-9), sold in France by the company Bayer; isododecane, sold in France by the company Bayer;
 or of a vegetable oil, or of a mixture of vegetable oils, such as squalane which is identified in Chemical Abstracts by the number RN=111–01–3 and which is a mixture of hydrocarbons containing more than 80% by weight of 2,6,10,15,19,23-hexamethyltetracosane, or a vegetable oil of ester or triglyceride type, for instance coco-caprylate/caprate, for example DUB™ 810C provided by the company Dubois, or else jojoba oil;
 or of a mixture of several of these various oils.

The composition as previously defined generally comprises, for 100% by weight, from 5% to 50% by weight of oil.

According to one particular aspect, the constituent polyelectrolyte of the composition which is the subject of the present invention comprises a non-zero molar proportion of monomeric units resulting from the acid of formula ($I_1$):

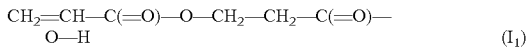
$$CH_2\!=\!CH\!-\!C(\!=\!O)\!-\!O\!-\!CH_2\!-\!CH_2\!-\!C(\!=\!O)\!-\!O\!-\!H \quad (I_1)$$

corresponding to formula (I) as previously defined, in which n represents a number equal to 1, in free or partially salified form.

According to another particular aspect, the constituent polyelectrolyte of the composition which is the subject of the present invention comprises a non-zero molar proportion of monomeric units resulting from a mixture of the acid of formula ($I_1$):

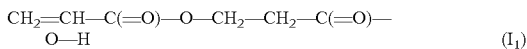
$$CH_2\!=\!CH\!-\!C(\!=\!O)\!-\!O\!-\!CH_2\!-\!CH_2\!-\!C(\!=\!O)\!-\!O\!-\!H \quad (I_1)$$

corresponding to formula (I) as previously defined, in which n represents a number equal to 1, and of the acid of formula ($I_2$):

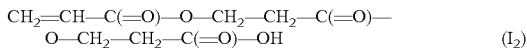
$$CH_2\!=\!CH\!-\!C(\!=\!O)\!-\!O\!-\!CH_2\!-\!CH_2\!-\!C(\!=\!O)\!-\!O\!-\!CH_2\!-\!CH_2\!-\!C(\!=\!O)\!-\!OH \quad (I_2)$$

corresponding to formula (I) as previously defined, in which n represents a number equal to 2, said acids being in free or partially salified form, in a ($I_1$)/($I_2$) molar ratio greater than 1 and more particularly greater than 1.5.

According to another particular aspect, the constituent polyelectrolyte of the composition which is the subject of the present invention comprises a non-zero molar proportion of monomeric units resulting from a mixture of the acid of formula ($I_1$):

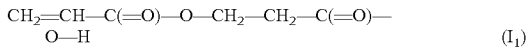
$$CH_2\!=\!CH\!-\!C(\!=\!O)\!-\!O\!-\!CH_2\!-\!CH_2\!-\!C(\!=\!O)\!-\!O\!-\!H \quad (I_1)$$

corresponding to formula (I) as previously defined, in which n represents a number equal to 1, of the acid of formula ($I_2$):

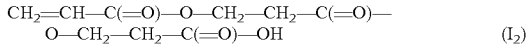
$$CH_2\!=\!CH\!-\!C(\!=\!O)\!-\!O\!-\!CH_2\!-\!CH_2\!-\!C(\!=\!O)\!-\!O\!-\!CH_2\!-\!CH_2\!-\!C(\!=\!O)\!-\!OH \quad (I_2)$$

corresponding to formula (I) as previously defined, in which n represents a number equal to 2, and of the acid of formula ($I_3$):

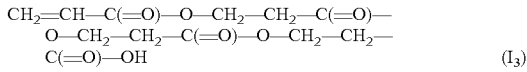
$$CH_2\!=\!CH\!-\!C(\!=\!O)\!-\!O\!-\!CH_2\!-\!CH_2\!-\!C(\!=\!O)\!-\!O\!-\!CH_2\!-\!CH_2\!-\!C(\!=\!O)\!-\!O\!-\!CH_2\!-\!CH_2\!-\!C(\!=\!O)\!-\!OH \quad (I_3)$$

corresponding to formula (I) as previously defined, in which n represents a number equal to 3, said acids being in free or partially salified form, in a ($I_1$)/($I_2$) molar ratio greater than 1 and more particularly greater than 1.5 and in a ($I_2$)/($I_3$) molar ratio greater than 1.5 and more particularly greater than or equal to 2.

According to one particular aspect, the constituent anionic polyelectrolyte of the inverse latex as defined above comprises, for 100 mol %:

- from 90 mol % to 99.5 mol % and more particularly from 95 mol % to 99 mol % of monomeric units resulting from free or partially salified acrylic acid;
- from 0.5 mol % to 10 mol % and more particularly from 1 mol % to 5 mol % of monomeric units resulting from the carboxylic acid of formula (I), which is free or partially salified.

According to another particular aspect of the present invention, the anionic polyelectrolyte as previously defined is crosslinked.

In the latter case, the crosslinking agent is chosen in particular from diethylenic or polyethylenic compounds, and most particularly from diallyloxyacetic acid or a salt thereof and in particular the sodium salt thereof, triallylamine, or salts thereof, trimethylolpropane triacrylate, ethylene glycol dimethacrylate, diethylene glycol diacrylate, diallylurea or methylenebis(acrylamide).

According to one particular aspect of the present invention, the crosslinking agent used is triallylamine or methylenebis(acrylamide).

The crosslinking agent is then generally used in the molar proportion, expressed relative to the monomers used, of from 0.005 mol % to 1 mol %.

According to another particular aspect of the present invention, the composition as previously defined also comprises an "oil-in-water" emulsifying system.

Said "oil-in-water (O/W) emulsifying system" consists either of a single surfactant or of a mixture of surfactants, on the condition that said surfactant or said mixture has an HLB value sufficiently high to induce an oil-in-water emulsion. Mention is made, for example, of:

- ethoxylated sorbitan esters, for instance sorbitan oleate polyethoxylated with 20 mol of ethylene oxide, sold by the company SEPPIC under the name Montanox™ 80 or sorbitan laurate polyethoxylated with 20 mol of ethylene oxide, sold by the company SEPPIC under the name Montanox™ 20;
- the castor oil polyethoxylated with 40 mol of ethylene oxide sold under the name Simulsol™ OL50;
- the decaethoxylated oleodecyl alcohol sold by the company SEPPIC under the name Simulsol™ OC 710;
- the heptaethoxylated lauryl alcohol sold under the name Simulsol™ P7; or
- the polyethoxylated sorbitan hexaoleates sold by the company SEPPIC under the name Simaline IE 400.

When it also comprises an "oil-in-water" emulsifying system, the composition as previously defined is then in the form of a self-invertible inverse latex which generally comprises from 1% by weight to 15% by weight of said "oil-in-water" emulsifying system.

The composition according to the invention can also contain various additives, such as complexing agents or chain limiters.

According to another particular aspect of the present invention, a subject thereof is a composition as previously defined, comprising from 15% to 60% by weight, and preferably from 25% to 40% by weight, of said anionic polyelectrolyte.

According to another particular aspect of the present invention, a subject thereof is a composition as previously defined, comprising more than 60% up to 80% by weight, and preferably more than 60% to 70% by weight, of said anionic polyelectrolyte.

The compounds of formula (I) in which n is equal to 1, called 4-oxa-5-oxohept-6-enoic acid or β-carboxyethyl acrylate, is a commercially available product. It is identified under the number CAS=24615-84-7.

According to another aspect of the present invention, a subject thereof is a process for preparing the composition as defined in any one of the preceding aspects, comprising the following steps:

- a step a) during which an aqueous solution comprising the monomers and the optional additives which are hydrophilic is emulsified in an oil phase comprising the monomers and the optional additives which are lipophilic in the presence of said water-in-oil emulsifying system;
- a step b) during which the polymerization reaction is initiated by introducing into the emulsion formed at the end of step a) a free-radical initiator and optionally a coinitiator, and then left to take place to obtain said composition in the form of an inverse latex.

During step b) of the process as defined, the polymerization reaction is generally initiated by an oxidation/reduction couple which generates hydrogen sulfite ($HSO_3$) ions, such as the cumene hydro-peroxide/sodium metabisulfite ($Na_2S_2O_5$)

couple or the cumene hydroperoxide/thionyl chloride (SOCl$_2$) couple, at a temperature of less than or equal to 10° C., if desired accompanied by a polymerization coinitiator, for instance azobis(isobutyronitrile), dilauroyl peroxide or sodium persulfate, and then carried out either quasiadiabatically up to a temperature greater than or equal to 50° C., or by controlling the temperature.

According to one particular aspect, the process as defined above also comprises a step c) during which said oil-in-water emulsifying system is added to the inverse latex formed at the end of step b), so as to obtain said composition in the form of a self-invertible inverse latex.

During step c) of the process as defined above, the addition of said oil-in-water emulsifying system is generally carried out at a temperature of less than or equal to 50° C.

According to one particular aspect, the process as defined also comprises a step $b_1$ during which the inverse latex resulting from step b) is concentrated so as to obtain said composition in the form of a concentrated inverse latex, before the implementation, where appropriate, of step c).

According to one particular aspect, the process as defined above also comprises a step $c_1$ during which the self-invertible inverse latex resulting from step c) is concentrated so as to obtain said composition in the form of a concentrated self-invertible inverse latex.

During step $b_1$ or step $c_1$ of the process as defined above, the concentrating of the medium is generally carried out by distillation until the desired content of anionic polyelectrolyte within the composition which is the subject of the present invention is achieved.

According to one particular aspect, the process as defined above also comprises a step d) during which the inverse latex resulting from step b), the concentrated inverse latex resulting from step b1), the self-invertible inverse latex resulting from step c) or the concentrated self-invertible inverse latex resulting from step c1) is spray-dried so as to form a powder of said anionic polyelectrolyte.

A subject of the invention is also a powder of the linear or crosslinked anionic polyelectrolyte, characterized in that it is obtained by means of the process as previously defined.

The anionic polyelectrolyte which is the subject of the present invention and also the inverse latexes and the self-invertible inverse latexes comprising same are advantageously used as thickeners and/or as emulsifiers/stabilizers in cosmetic or pharmaceutical compositions.

Consequently, according to another aspect, a subject of the invention is the use of the composition as previously defined or of the powder as previously defined, as a thickener and/or as an emulsifier in cosmetic or pharmaceutical compositions.

The powder or composition in the form of an optionally self-invertible inverse latex, which is the subject of the present invention, can be formulated in cosmetic or pharmaceutical formulas such as mousses, gels, lotions, sprays, shampoos, conditioners, hand and body lotions, and sunscreens, and more generally in care products.

In the case of hair treatment or upkeep, such cosmetic or pharmaceutical compositions are usually in the form of shampoos, of emulsions, of microemulsions and, in particular in the case of conditioners, of vaporizable emulsions.

According to a final aspect, a subject of the invention is a cosmetic or pharmaceutical composition characterized in that it contains, as emulsifier and/or thickener, an effective amount of the composition as previously defined or of the powder as previously defined.

The term "effective amount" is intended to mean a weight proportion of between approximately 1% and approximately 10% by weight of the composition as previously defined and approximately 0.2% by weight to approximately 5% of the powder as previously defined.

The following examples illustrate the present invention without, however, limiting it.

Example A

Self-Invertible Inverse Latex of a Homopolymer of Acrylic Acid which is Partially Salified in the Form of a Sodium Salt, Crosslinked with Triallylamine (Prior Art)

Preparation of the Self-Invertible Inverse Latex
An oil phase is prepared by mixing:
  261 g of Marcol™ 52,
  15.5 g of Montane™ 80 VG, and
  3.5 g of Montanox™ 81: 3.5 g.
An aqueous phase is prepared by introducing:
  203 g of glacial acrylic acid,
  188 g of an aqueous solution containing 48% by weight of sodium hydroxide,
  0.45 g of Versenex™ 80,
  0.77 g of triallylamine, and then the weight is brought to 653 g with deionized water.
The aqueous phase is introduced into the oil phase and emulsification is carried out using an Ultra Turrax™ device.
After having left the system to stir and sparging with nitrogen, it is cooled to 10° C. and 10 cm$^3$ of a solution containing 0.268% by weight of cumene hydro-peroxide in Marcol™ 52 are added thereto, followed, gradually, by 20 g of an aqueous solution containing 0.54% by weight of sodium metabisulfite.
The temperature is left to rise in the reaction medium to 80° C. and then the reaction is left to take place for one hour.
  30 g of Montanox™ 80 are introduced into the final inverse latex obtained.
Viscosimetric analysis of the self-invertible inverse latex obtained
Viscosity of an aqueous dispersion of 3% by weight of the self-invertible inverse latex: 55 800 mPas (Brookfield™ RVT, spindle 6, speed: 5 revolutions per minute).
Viscosity of an aqueous dispersion containing 0.1% by weight of sodium chloride and 3% by weight of the self-invertible inverse latex:
3200 mPas (Brookfield™ RVT, spindle 3, 5 revolutions per minute).

Example 1

Self-invertible inverse latex of a copolymer of acrylic acid/β-carboxyethyl acrylate which is partially salified in the form of a sodium salt, crosslinked with triallylamine, in Marcol™ 52 (composition 1)
Preparation of the Self-Invertible Inverse Latex
An oil phase is prepared by mixing:
  261 g of Marcol™ 52,
  15.5 g of Montane™ 80 VG, and
  3.5 g of Montanox™ 81: 3.5 g.
An aqueous phase is prepared by introducing:
  186 g of glacial acrylic acid,
  17.3 g of β-carboxyethyl acrylate sold by the company Bimax under the name Beta-C™,
  188 g of an aqueous solution containing 48% by weight of sodium hydroxide,
  0.45 g of Versenex™ 80,
  0.77 g of triallylamine, and then the weight is brought to 653 g with deionized water.
The aqueous phase is introduced into the oil phase and emulsification is carried out using an Ultra Turrax™ device.

After having left the system to stir and sparging with nitrogen, it is cooled to 10° C. and 10 cm³ of a solution containing 0.268% by weight of cumene hydro-peroxide in Marcol™ 52 are added thereto, followed, gradually, by 20 g of an aqueous solution containing 0.54% by weight of sodium metabisulfite.

The temperature is left to rise in the reaction medium to 80° C. and then the reaction is left to take place for one hour. 30 g of Montanox™ 80 are introduced into the final inverse latex obtained.

Viscosimetric Analysis of the Self-Invertible Inverse Latex Obtained

Viscosity of an aqueous dispersion of 3% by weight of the self-invertible inverse latex: 80 400 mPas (Brookfield™ RVT, spindle 6, speed: 5 revolutions per minute).

Viscosity of an aqueous dispersion containing 0.1% by weight of sodium chloride and 3% by weight of the self-invertible inverse latex:
5600 mPas (Brookfield™ RVT, spindle 3, 5 revolutions per minute).

This analysis makes it possible to demonstrate a more accentuated thickening power than that of the self-invertible inverse latex of example A, which is due to the presence of monomeric units resulting from β-carboxyethyl acrylate. A slight improvement in the salt content should also be noted.

Example 2

Self-Invertible Inverse Latex of a Copolymer of Acrylic Acid/β-Carboxyethyl Acrylate which is Partially Salified in the Form of a Sodium Salt, Crosslinked with Triallylamine, in Squalane (Composition 2)

The process is carried out as in example 1, with the Marcol™ 52 being replaced with Squalane™ VG. The expected self-invertible inverse latex is obtained.

Example 3

Self-Invertible Inverse Latex of a Copolymer of acrylic acid/β-carboxyethyl acrylate which is partially salified in the form of a sodium salt, crosslinked with triallylamine, in Isopar™ M (Composition 3)

The process is carried out as in example 1, with the Marcol™ 52 being replaced with Isopar™ M. The expected self-invertible inverse latex is obtained.

Example 4

Powder of Copolymer of Acrylic Acid/β-Carboxyethyl Acrylate which is Partially Salified in the Form of a Sodium Salt, Crosslinked with Triallylamine The self-invertible inverse latex obtained in the previous example is concentrated by distillation, and then spray-dried.

Examples of Formulations

Example 5

Care Cream

| | |
|---|---|
| Cyclomethicone: | 10% |
| Composition 1: | 4% |
| Montanov™ 68: | 4.50% |
| Preservative: | 0.65% |
| Lysine: | 0.025% |
| EDTA (disodium salt): | 0.05% |
| Xanthan gum: | 0.20% |
| Glycerol: | 3% |
| Water: | qs 100% |

Example 6

Care Cream

| | |
|---|---|
| Cyclomethicone: | 10% |
| Composition 2: | 4% |
| Montanov™ 68: | 4.5% |
| Perfluoropolymethyl isopropyl ether: | 0.5% |
| Preservative: | 0.65% |
| Lysine: | 0.025% |
| EDTA (disodium salt): | 0.05% |
| Pemulen™ TR: | 0.2% |
| Glycerol: | 3% |
| Water: | qs 100% |

Example 7

Aftershave Balm

| | FORMULA | |
|---|---|---|
| A | Composition 3: | 3% |
| | Water: | q.s. 100% |
| B | Micropearl™ M 100: | 5.0% |
| | Sepicide™ CI: | 0.50% |
| | Fragrance: | 0.20% |
| | 95° ethanol: | 10.0% |
| PROCEDURE: Add B to A. | | |

Example 8

Satin Body Emulsion

| | FORMULA | |
|---|---|---|
| A | Simulsol™ 165: | 5.0% |
| | Lanol™ 1688: | 8.50% |
| | Shea butter: | 2% |
| | Liquid paraffin: | 6.5% |
| | Lanol™ 14M: | 3% |
| | Lanol™ S: | 0.6% |
| B | Water: | 66.2% |
| C | Micropearl™ M 100: | 5% |
| D | Powder of example 4: | 1% |
| E | Sepicide™ CI: | 0.3% |
| | Sepicide™ HB: | 0.5% |
| | Monteine™ CA: | 1% |
| | Fragrance: | 0.20% |
| | Vitamin E acetate: | 0.20% |
| | Sodium pyrrolidinonecarboxylate: | 1% (moisturizer) |

PROCEDURE: Add C to B, emulsify B in A at 70° C., then add D at 60° C. and then E at 30° C.

Example 9

Body Milk

| | FORMULA | |
|---|---|---|
| A | Simulsol ™ 165: | 5.0% |
| | Lanol ™ 1688: | 12.0% |
| | Lanol ™ 14M: | 2.0% |
| | Cetyl alcohol: | 0.3% |
| | Schercemol ™ OP: | 3% |
| B | Water: | q.s. 100% |
| C | Composition 1: | 0.35% |
| D | Sepicide ™ CI: | 0.2% |
| | Sepicide ™ HB: | 0.5% |
| | Fragrance: | 0.20% |

PROCEDURE: Emulsify B in A at about 75° C.; add C at about 60° C. and then D at about 30° C.

Example 10

O/W Cream

| | FORMULA | |
|---|---|---|
| A | Simulsol ™ 65: | 5.0% |
| | Lanol ™ 1688: | 20.0% |
| | Lanol ™ P: | 1.0% (additive with stabilizing effect) |
| B | Water: | q.s. 100% |
| C | Composition 1: | 2.50% |
| D | Sepicide ™ CI: | 0.20% |
| | Sepicide ™ HB: | 0.30% |

PROCEDURE: Introduce B into A at about 75° C.; add C at about 60° C. and then D at about 45° C.

Example 11

Nongreasy Antisun Gel

| | FORMULA | |
|---|---|---|
| A | Composition 3: | 3.00% |
| | Water: | 30% |
| B | Sepicide ™ C: | 0.20% |
| | Sepicide ™ HB: | 0.30% |
| | Fragrance: | 0.10% |
| C | Dye: | q.s. |
| | Water: | 30% |
| D | Micropearl ™ M 100: | 3.00% |
| | Water: | q.s. 100% |
| E | Silicone oil: | 2.00% |
| | Parsol ™ MCX: | 5.00% |

PROCEDURE: Introduce B into A; add C then D then E.

Example 12

Antisun Milk

| | FORMULA | |
|---|---|---|
| A | Sepiperl ™ N: | 3.0% |
| | Sesame oil: | 5.0% |
| | Parsol ™ MCX: | 5.0% |
| | λ carrageenan: | 0.10% |
| B | Water: | q.s. 100% |
| C | Powder of example 4: | 0.80% |
| D | Fragrance: | q.s. |
| | Preservative: | q.s. |

PROCEDURE: Emulsify B in A at 75° C. then add C at about 60° C., then D at about 30° C. and adjust the pH if necessary.

Example 13

Massage Gel

| | FORMULA | |
|---|---|---|
| A | Composition 3: | 3.5% |
| | Water: | 20.0% |
| B | Dye: | 2 drops/100 g |
| | Water: | q.s. |
| C | Alcohol: | 10% |
| | Menthol: | 0.10% |
| D | Silicone oil: | 5.0% |

PROCEDURE: Add B to A; then add C to the mixture, then D.

Example 14

Massage Care Gel

| | FORMULA | |
|---|---|---|
| A | Composition 1: | 3.00% |
| | Water: | 30% |
| B | Sepicide ™ CI: | 0.20% |
| | Sepicide ™ HB: | 0.30% |
| | Fragrance: | 0.05% |
| C | Dye: | q.s. |
| | Water: | q.s. 100% |
| D | Micropearl ™ SQL: | 5.0% |
| | Lanol ™ 1688: | 2% |

PROCEDURE: Prepare A; add B, then C, then D.

Example 15

Radiance Gel

| | FORMULA | |
|---|---|---|
| A | Composition 2: | 4% |
| | Water: | 30% |
| B | Elastin ™ HPM: | 5.0% |
| C | Micropearl ™ M 100: | 3% |
| | Water: | 5% |
| D | Sepicide ™ CI: | 0.2% |
| | Sepicide ™ HB: | 0.3% |
| | Fragrance: | 0.06% |
| | 50% sodium pyrrolidinonecarboxylate: | 1% |
| | Water: | q.s. 100% |

PROCEDURE: Prepare A; add B, then C, then D.

Example 16

Body Milk

| | FORMULA | |
|---|---|---|
| A | Sepiperl ™ N: | 3.0% |
| | Glyceryl triheptonate: | 10.0% |
| B | Water: | q.s. 100% |
| C | Powder of example 4: | 1.0% |
| D | Fragrance: | q.s. |
| | Preservative: | q.s. |

PROCEDURE: Melt A at about 75° C. Emulsify B in A at 75° C. then add C at about 60° C., then D.

Example 17

Makeup-Removing Emulsion with Sweet Almond Oil

| FORMULA | |
|---|---|
| Montanov ™ 68: | 5% |
| Sweet almond oil: | 5% |
| Water: | q.s. 100% |
| Powder of example 4: | 0.3% |
| Glycerol: | 5% |
| Preservative: | 0.2% |
| Fragrance: | 0.3% |

Example 18

Moisturizing Cream for Greasy Skin

| FORMULA | |
|---|---|
| Montanov ™ 68: | 5% |
| Cetylstearyl octanoate: | 8% |
| Octyl palmitate: | 2% |
| Water: | q.s. 100% |
| Composition 1: | 0.6% |
| Micropearl ™ M 100: | 3.0% |
| Mucopolysaccharides: | 5% |
| Sepicide ™ HB: | 0.8% |
| Fragrance: | 0.3% |

Example 19

Alcohol-Free Soothing Aftershave Balm

| FORMULA | |
|---|---|
| Mixture of lauryl amino acids: | 0.1% to 5% |
| Magnesium potassium aspartate: | 0.002% to 0.5% |
| Lanol ™ 99: | 2% |
| Sweet almond oil: | 0.5% |
| Water: | q.s. 100% |
| Composition 1: | 3% |
| Sepicide ™ HB: | 0.3% |
| Sepicide ™ CI: | 0.2% |
| Fragrance: | 0.4% |

Example 20

Cream with AHA for Sensitive Skin

| FORMULA | |
|---|---|
| Mixture of lauryl amino acids: | 0.1% to 5% |
| Magnesium potassium aspartate: | 0.002% to 0.5% |
| Lanol ™ 99: | 2% |
| Montanov ™ 68: | 5.0% |
| Water: | q.s. 100% |
| Composition 3: | 1.50% |
| Gluconic acid: | 1.50% |
| Triethanolamine: | 0.9% |
| Sepicide ™ HB: | 0.3% |
| Sepicide ™ CI: | 0.2% |
| Fragrance: | 0.4% |

Example 21

Aftersun Soothing Care Product

| FORMULA | |
|---|---|
| Mixture of lauryl amino acids: | 0.1% to 5% |
| Magnesium potassium aspartate: | 0.002% to 0.5% |
| Lanol ™ 99: | 10.0% |
| Water: | q.s. 100% |
| Composition 2: | 2.50% |
| Sepicide ™ HB: | 0.3% |
| Sepicide ™ CI: | 0.2% |
| Fragrance: | 0.4% |
| Dye: | 0.03% |

Example 22

Makeup-Removing Milk

| FORMULA | |
|---|---|
| Sepiperl ™ N: | 3% |
| Primol ™ 352: | 8.0% |
| Sweet almond oil: | 2% |
| Water: | q.s. 100% |
| Composition 1: | 0.8% |
| Preservative: | 0.2% |

Example 23

Body Milk

| FORMULA | |
|---|---|
| Sepiperl ™ N: | 3.5% |
| Lanol ™ 37T: | 8.0% |
| Solagum ™ L: | 0.05% |
| Water: | q.s. 100% |
| Benzophenone: | 2.0% |
| Dimethicone 350 cPs: | 0.05% |
| Powder of example 4: | 0.8% |
| Preservative: | 0.2% |
| Fragrance: | 0.4% |

Example 24

Fluid Emulsion at Alkaline pH

| Marcol ™ 82: | 5.0% |
|---|---|
| NaOH: | 10.0% |
| Water: | q.s. 100% |
| Composition 1: | 1.5% |

Example 25

Fluid Foundation

| FORMULA | |
|---|---|
| Simulsol ™ 165: | 5.0% |
| Lanol ™ 84D: | 8.0% |
| Lanol ™ 99: | 5.0% |
| Water: | q.s. 100% |
| Mineral fillers and pigments: | 10.0% |
| Composition 3: | 1.2% |
| Preservative: | 0.2% |
| Fragrance: | 0.4% |

Example 26

Antisun Milk

| FORMULA | |
|---|---|
| Sepiperl ™ N: | 3.5% |
| Lanol ™ 37T: | 10.0% |
| Parsol ™ NOX: | 5.0% |
| Eusolex ™ 4360: | 2.0% |
| Water: | q.s. 100% |
| Composition 1: | 1.8% |
| Preservative: | 0.2% |
| Fragrance: | 0.4% |

Example 27

Eye Contour Gel

| FORMULA | |
|---|---|
| Composition 2: | 2.0% |
| Fragrance: | 0.06% |
| Sodium pyrrolidinonecarboxylate: | 0.2% |
| Dow Corning ™ 245 Fluid: | 2.0% |
| Water: | q.s. 100% |

Example 28

Leave-In Care Composition

| FORMULA | |
|---|---|
| Composition 1: | 1.5% |
| Fragrance: | q.s. |
| Preservative: | q.s. |
| Dow Corning ™ X2 8360: | 5.0% |
| Dow Corning ™ Q2 1401: | 15% |
| Water: | q.s. 100% |

Example 29

Slimming Gel

| Composition 3: | 5% |
|---|---|
| Ethanol: | 30% |
| Menthol: | 0.1% |
| Caffeine: | 2.5% |
| Extract of *ruscus*: | 2% |
| Extract of *ivy*: | 2% |
| Sepicide ™ HB: | 1% |
| Water: | q.s. 100% |

Example 30

Alcohol-Free Soothing Aftershave Balm

| | FORMULA | |
|---|---|---|
| A | Lipacide ™ PVB: | 1.0% |
| | Lanol ™ 99: | 2.0% |
| | Sweet almond oil: | 0.5% |
| B | Composition 1: | 3.5% |
| C | Water: | q.s. 100% |
| D | Fragrance: | 0.4% |
| | Sepicide ™ HB: | 0.4% |
| | Sepicide ™ CI: | 0.2% |

Example 31

Refreshing Aftershave Gel

| | FORMULA | |
|---|---|---|
| A | Lipacide ™ PVB: | 0.5% |
| | Lanol ™ 99: | 5.0% |
| | Composition 1: | 2.5% |
| B | Water: | q.s. 100% |
| C | Micropearl ™ LM: | 0.5% |
| | Fragrance: | 0.2% |
| | Sepicide ™ HB: | 0.3% |
| | Sepicide ™ CI: | 0.2% |

Example 32

Care Product for Greasy Skin

| | FORMULA | |
|---|---|---|
| A | Micropearl ™ M310: | 1.0% |
| | Composition 1: | 5.0% |
| | Octyl isononanoate: | 4.0% |
| B | Water: | q.s. 100% |
| C | Sepicontrol ™ A5: | 4.0% |
| | Fragrance: | 0.1% |
| | Sepicide ™ HB: | 0.3% |
| | Sepicide ™ CI: | 0.2% |
| D | Capigel ™ 98: | 0.5% |
| | Water: | 10% |

Example 33

Cream with AHA

| | FORMULA | |
|---|---|---|
| A | Montanov ™ 68: | 5.0% |
| | Lipacide ™ PVB: | 1.05% |
| | Lanol ™ 99: | 10.0% |
| B | Water: | q.s. 100% |
| | Gluconic acid: | 1.5% |
| | TEA (triethanolamine): | 0.9% |
| C | Composition 1: | 1.5% |
| D | Fragrance: | 0.4% |
| | Sepicide ™ HB: | 0.2% |
| | Sepicide ™ CI: | 0.4% |

Example 34

Nongreasy Self-Tanning Product for the Face and Body

| | FORMULA | |
|---|---|---|
| A | Lanol ™ 2681: | 3.0% |
| | Composition 3: | 2.5% |
| B | Water: | q.s. 100% |
| | Dihydroxyacetone: | 3.0% |
| C | Fragrance: | 0.2% |
| | Sepicide ™ HB: | 0.8% |
| | NaOH (sodium hydroxide): | qs pH = 5% |

Example 35

Antisun Milk with Monoi Oil

| | FORMULA | |
|---|---|---|
| A | Monoi oil: | 10% |
| | Lipacide ™ PVB: | 0.5% |
| | Composition 2: | 2.2% |
| B | Water: | q.s. 100% |
| C | Fragrance: | 0.1% |
| | Sepicide ™ HB: | 0.3% |
| | Sepicide ™ CI: | 0.1% |
| | Octyl methoxycinnamate: | 4.0% |

Example 36

Facial Antisun Care Product

| | FORMULA | |
|---|---|---|
| A | Cyclomethicone and dimethiconol: | 4.0% |
| | Composition 1: | 3.5% |
| B | Water: | q.s. 100% |
| C | Fragrance: | 0.1% |
| | Sepicide ™ HB: | 0.3% |
| | Sepicide ™ CI: | 0.21% |
| | Octyl methoxycinnamate: | 5.0% |
| | Titanium mica: | 2.0% |
| | Lactic acid: | q.s. pH = 6.5 |

Example 37

No-Sun Tanning Emulsion

| | FORMULA | |
|---|---|---|
| A | Lanol ™ 99: | 15% |
| | Montanov ™ 68: | 5.0% |
| | Octyl para-methoxycinnamate: | 3.0% |
| B | Water: | q.s. 100% |
| | Dihydroxyacetone: | 5.0% |
| | Monosodium phosphate: | 0.2% |
| C | Powder of example 4: | 0.5% |
| D | Fragrance: | 0.3% |
| | Sepicide ™ HB: | 0.8% |
| | NaOH: | q.s. pH = 5. |

Example 38

Gloss Gel

| | |
|---|---|
| Powder of example 4: | 1.5% |
| Volatile silicone: | 25% |
| Monopropylene glycol: | 25% |
| Demineralized water: | 10% |
| Glycerol: | q.s. 100% |

Example 39

Slimming Gel

| | |
|---|---|
| Composition 1: | 1.5% |
| Isononyl isononanoate: | 2% |
| Caffeine: | 5% |
| Ethanol: | 40% |
| Micropearl ™ LM: | 2% |
| Demineralized water: | q.s. 100% |
| Preservative, fragrance: | qs |

Example 40

Makeup-Removing Milk

| | |
|---|---|
| Simulsol ™ 165: | 4% |
| Montanov ™ 202: | 1% |
| Triglyceride caprylate-caprate: | 15% |
| Pecosil ™ DCT: | 1% |
| Demineralized water: | qs |
| Capigel ™ 98: | 0.5% |
| Composition 3: | 1% |
| Proteol ™ OAT: | 2% |
| NaOH: | qs pH 7 |

Example 41

Antisun Cream

| | |
|---|---|
| Simulsol ™ 165 | 3% |
| Montanov ™ 202 | 2% |
| $C_{12}$-$C_{15}$ benzoate | 8% |
| Pecosil ™ PS 100 | 2% |
| Dimethicone | 2% |
| Cyclomethicone | 5% |
| Octyl methoxycinnamate | 6% |
| Benzophenone-3 | 4% |
| Titanium oxide | 8% |
| Xanthan gum | 0.2% |
| Butylene glycol | 5% |
| Demineralized water | q.s. 100% |
| Composition 2 | 1.5% |
| Preservative, fragrance | qs |

Example 42

Care Gel for Combination Skin

| | |
|---|---|
| Composition 2 | 4% |
| Plant squalane | 5% |
| Dimethicone | 1.5% |
| Sepicontrol ™ A5 | 4% |
| Xanthan gum | 0.3% |
| Water | q.s. 100% |
| Preservative, fragrance | qs |

Example 43

Perfumed Body Mask

| | |
|---|---|
| Composition 1: | 1.5% |
| Cyclomethicone: | 5% |
| Fragrance: | 2% |
| Micropearl ™ M100: | 5% |
| Glycerol: | 5% |
| Demineralized water: | q.s. 100% |

Example 44

Cream with Vitamins

| | |
|---|---|
| Simulsol ™ 165: | 5% |
| Montanov ™ 202: | 1% |
| Caprylic/capric triglycerides: | 20% |
| Vitamin A palmitate: | 0.2% |
| Vitamin E acetate: | 1% |
| Micropearl ™ M305: | 1.5% |
| Powder of example 4: | 0.7% |
| Water: | q.s. 100% |
| Preservative, fragrance: | qs |

Example 45

Antistress Hair Care Product

| Formula | |
|---|---|
| Phase A | |
| Water: | qs 100% |
| Xanthan gum: | 0.50% |
| Phase B | |
| Sepicap ™ MP: | 3.00% |
| Phase C | |
| Composition 1: | 4.00% |
| Phase D | |
| Butylene glycol: | 5.00% |
| Lanol ™ 99: | 5.00% |
| Sepicide ™ HB: | 0.30% |
| Sepicide ™ CI: | 0.20% |
| Fragrance: | 0.20% |

Procedure: Disperse the xanthan gum in the water with a deflocculator. Then add Sepicap ™ MP, then composition 1; disperse it and then add the ingredients of phase D.

Example 46

Restructuring Cream Mask for Stressed and Embrittled Hair

| Formula | |
|---|---|
| Phase A | |
| Montanov ™ 82: | 3.00% |
| Lanol ™ P: | 6.00% |
| Amonyl ™ DM: | 1.00% |
| Isostearyl isononanoate: | 5.00% |
| Powder of example 4: | 2.50% |
| Phase B | |
| Water: | q.s. 100% |
| Phase C | |
| Sepicap ™ MP: | 3.00% |
| Sepicide ™ HB: | 0.30% |
| Sepicide ™ CI: | 0.20% |

Procedure: Melt phase A at 75° C. Heat phase B to 75° C. Emulsify A in B. At about 40° C., introduce the constituents of phase C.

Example 47

Purifying Facial Gel

| Formula | |
|---|---|
| Phase A | |
| Montaline ™ C 40: | 7.00% |
| Pearlescent base 2078: | 5.00% |
| Composition 1: | 2.00% |
| Phase B | |
| Water: | q.s. 100% |

Example 48

Coloring Shampoo

| Formula | |
|---|---|
| Phase A | |
| Montaline ™ C 40: | 15.00% |
| Disodium cocoamphoacetate: | 5.00% |
| Cetrimonium chloride: | 1.00% |
| Sepiperl ™ N: | 3.00% |
| Composition 3: | 3.00% |
| Phase B | |
| Color | qs |
| Water | q.s. 100% |

Example 49

Hair Lotion

| | |
|---|---|
| Butylene glycol: | 3.0% |
| Composition 1: | 3.0% |
| Simulsol ™ 1293: | 3.0% |
| Lactic acid: | q.s. ph = 6 |
| Sepicide ™ HB: | 0.2% |
| Sepicide ™ CI: | 0.3% |
| Fragrance: | 0.3% |
| Water: | q.s. 100% |

Example 50

Protecting and Relaxing Shampoo

| | |
|---|---|
| Amonyl ™ 675 SB: | 5.0% |
| Sodium lauroyl ether sulfate at 28%: | 35.0% |
| Powder of example 4: | 3.0% |
| Sepicide ™ HB: | 0.5% |
| Sepicide ™ CI: | 0.3% |
| Sodium hydroxide: | q.s. pH = 7.2 |
| Fragrance: | 0.3% |
| Dye (FDC blue 1/yellow 5): | q.s. |
| Water: | q.s. 100% |

Example 51

Leave-On Protector; Antistress Hair Care Product

| | |
|---|---|
| Ketrol ™ T: | 0.5% |
| Mixture of cocoyl amino acids: | 3.0% |
| Butylene glycol: | 5.0% |
| DC 1501: | 5.0% |
| Composition 2: | 4.0% |
| Sepicide ™ HB: | 0.5% |
| Sepicide ™ CI: | 0.3% |
| Fragrance: | 0.3% |
| Water: | q.s. 100% |

Montanov™ 68 (cetearyl glucoside) is a self-emulsifying composition as described in WO 92/06778, sold by the company SEPPIC.

Montanov™ 82 is an emulsifier based on cetearyl alcohol and cocoyl glucoside.

Montanov™ 202 is an APG/fatty alcohol composition as described in WO 98/47610, sold by the company SEPPIC.

Micropearl™ LM is a mixture of squalane, poly(methyl methacrylate) and menthol, sold by the company SEPPIC.

Micropearl™ M 100 is an ultrafine powder with a very soft feel and a matting action, sold by the company Matsumo.

Micropearl™ SQL is a mixture of microparticles containing squalane, which is released under the action of massaging; it is sold by the company Matsumo.

Sepicide™ HB, which is a mixture of phenoxyethanol, methylparaben, ethylparaben, propylparaben and butyl-paraben, is a preservative sold by the company SEPPIC.

Sepicide™ CI, imidazolidine urea, is a preservative sold by the company SEPPIC.

Pemulen™ TR is an acrylic polymer sold by Goodrich.

Simulsol™ 165 is self-emulsifying glyceryl stearate sold by the company SEPPIC.

Lanol™ 14M and Lanol™ S are consistency factors sold by the company SEPPIC.

Lanol™ 84D is dioctyl malate sold by the company SEPPIC.

Lanol™ 99 is isononyl isononanoate sold by the company SEPPIC.

Lanol™ 37T is glyceryl triheptanoate, sold by the company SEPPIC.

Lanol™ P is an additive with a stabilizing effect, sold by the company SEPPIC.

Lanol™ 1688 is an emollient ester with a nongreasy effect, sold by the company SEPPIC.

Lanol™ 2681 is a coconut caprylate/caprate mixture, sold by the company SEPPIC.

Monteine™ CA is a moisturizer sold by the company SEPPIC.

Schercemol™ OP is an emollient ester with a nongreasy effect.

Parsol™ MCX is octyl para-methoxycinnamate, sold by the company Givaudan.

Sepiperl™ N is a pearlescent agent, sold by the company SEPPIC, based on a mixture of alkyl polyglucosides such as those described in WO 95/13863.

Solagum™ L is a carrageenan sold by the company SEPPIC. Marcol™ 82 is a liquid paraffin sold by the company Exxon.

Parsol™ NOX is a sunscreen sold by the company Givaudan.

Eusolex™ 4360 is a sunscreen sold by the company Merck.

Dow Corning™ 245 Fluid is cyclomethicone, sold by the company Dow Corning.

Lipacide™ PVB is an acylated wheat protein hydrolyzate sold by the company SEPPIC.

Sepicontrol™ A5 is a mixture of capryloyl glycine, sarcosine and extract of Cinnamon zylanicum, sold by the company SEPPIC, such as those described in international patent application PCT/FR98/01313 filed on Jun. 23, 1998.

Capigel™ 98 is an acrylic copolymer sold by the company SEPPIC.

The definitions of the commercial products used in the examples are the following:

Montaline™ C40: (cocamoniumcarbamoyl chloride) sold by SEPPIC.

Sepiperl™ N: (cocoylglucoside/cocoyl alcohol) sold by SEPPIC.

Amonyl™ DM: (quaternium 82) sold by SEPPIC.

Sepicap™ MP: (sodium cocoyl amino acids/potassium dimethicone copolyol panthenyl phosphate) sold by SEPPIC.

Simulsol™ 1293 is hydrogenated and ethoxylated castor oil, with an ethoxylation index equal to 40, sold by the company SEPPIC.

Ketrol™ T is xanthan gum sold by the company Kelco. DC1501 is a mixture of cyclopentasiloxane and dimethiconol, sold by the company Dow Chemical.

The invention claimed is:

1. A composition comprising:
   an oil phase;
   an aqueous phase;
   at least one water-in-oil emulsifying system; and
   a linear, branched or crosslinked anionic polyelectrolyte, comprising:
   a) from 90 mol % to 99.5 mol % of monomeric units resulting from acrylic acid in free or partially salified form, and
   b) a non-zero molar proportion of from 0.5 mol % to 10 mol % of monomeric units resulting from the acid of formula (I):

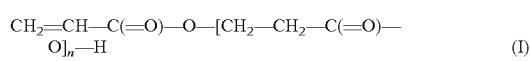

in which n represents a number greater than or equal to 1 and less than or equal to 5, or from a mixture of acids of formula (I), in free or partially salified form,
   wherein said composition is in the form of an inverse latex.

2. The composition as defined in claim 1, in which said anionic polyelectrolyte comprises, for 100 mol %:
   from 95 mol % to 99 mol % of monomeric units resulting from free or partially salified acrylic acid;
   from 1 mol % to 5 mol % of monomeric units resulting from the carboxylic acid of formula (I), which is free or partially salified.

3. The composition as defined in claim 1, in which said anionic polyelectrolyte comprises a non-zero molar proportion of monomeric units resulting from a mixture of the acid of formula (I₁):

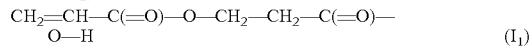

corresponding to formula (I) as previously defined, in which n represents a number equal to 1, and of the acid of formula (I₂):

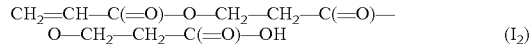

corresponding to formula (I) as previously defined, in which n represents a number equal to 2, said acids being in free or partially salified form, in a (I₁)/(I₂) molar ratio greater than 1.

4. The composition as defined in claim 1, in which said anionic polyelectrolyte comprises a non-zero molar proportion of monomeric units resulting from a mixture of the acid of formula (I₁):

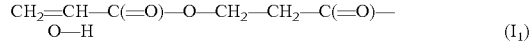

corresponding to formula (I) as previously defined, in which n represents a number equal to 1, of the acid of formula (I₂):

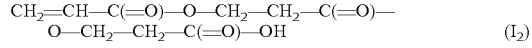

corresponding to formula (I) as previously defined, in which n represents a number equal to 2, and of the acid of formula (I₃):

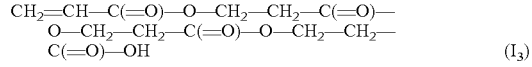

corresponding to formula (I) as previously defined, in which n represents a number equal to 3, said acids being in free or partially salified form, in a (I₁)/(I₂) molar ratio greater than 1 and in a (I₂)/(I₃) molar ratio greater than 1.5.

5. The composition as defined in claim 1, in which the anionic polyelectrolyte as previously defined is crosslinked.

6. The composition as defined in claim 1, comprising from 15% to 80% by weight of said anionic polyelectrolyte.

7. The composition as defined in claim 1, also comprising an "oil-in-water" emulsifying system.

8. A cosmetic or pharmaceutical composition characterized in that it contains, as emulsifier and/or thickener, an effective amount as defined in claim 1.

9. The composition as defined in claim 3, wherein the (I₁)/(I₂) molar ratio is greater than 1.5.

10. The composition as defined in claim 4, wherein the (I₁)/(I₂) molar ratio is greater than 1.5.

11. The composition as defined in claim 4, wherein the (I₂)/(I₃) molar ratio is greater than or equal to 2.

* * * * *